United States Patent
Carbunaru et al.

(10) Patent No.: US 9,446,231 B2
(45) Date of Patent: Sep. 20, 2016

(54) NEUROSTIMULATION SYSTEM AND METHOD FOR COMPOUNDING CURRENT TO MINIMIZE CURRENT SOURCES

(75) Inventors: Rafael Carbunaru, Valley Village, CA (US); Kristen Jaax, Santa Clarita, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1179 days.

(21) Appl. No.: 12/952,738

(22) Filed: Nov. 23, 2010

(65) Prior Publication Data

US 2011/0125223 A1     May 26, 2011

Related U.S. Application Data

(60) Provisional application No. 61/263,652, filed on Nov. 23, 2009.

(51) Int. Cl.
| | |
|---|---|
| A61N 1/36 | (2006.01) |
| A61N 1/05 | (2006.01) |
| A61N 1/372 | (2006.01) |
| A61N 1/08 | (2006.01) |

(52) U.S. Cl.
CPC ......... *A61N 1/0551* (2013.01); *A61N 1/36185* (2013.01); *A61N 1/37288* (2013.01); *A61N 2001/083* (2013.01)

(58) Field of Classification Search
USPC .......................................................... 607/66
See application file for complete search history.

(56) References Cited

U.S. PATENT DOCUMENTS

| | | | |
|---|---|---|---|
| 6,181,969 B1 | 1/2001 | Gord | |
| 6,516,227 B1* | 2/2003 | Meadows et al. | 607/46 |
| 6,895,280 B2 | 5/2005 | Meadows et al. | |
| 6,993,384 B2 | 1/2006 | Bradley et al. | |
| 7,239,920 B1 | 7/2007 | Thacker et al. | |
| 7,317,948 B1 | 1/2008 | King et al. | |
| 7,539,538 B2 | 5/2009 | Parramon et al. | |
| 8,131,357 B2 | 3/2012 | Bradley et al. | |
| 2003/0139781 A1 | 7/2003 | Bradley et al. | |
| 2005/0267546 A1 | 12/2005 | Parramon et al. | |
| 2006/0224222 A1 | 10/2006 | Bradley et al. | |
| 2007/0100399 A1 | 5/2007 | Parramon et al. | |

OTHER PUBLICATIONS

Office Action dated Jun. 20, 2012 in U.S. Appl. No. 12/952,845, filed Nov. 23, 2010, inventor: Rafael Carbunaru, (17 pages).

\* cited by examiner

*Primary Examiner* — William Levicky
(74) *Attorney, Agent, or Firm* — Schwegman Lundberg & Woessner, P.A.

(57) ABSTRACT

A neurostimulation system and method of providing therapy to a patient implanted with a plurality of electrodes using a plurality of electrical sources is provided. A source-electrode coupling configuration is determined from the electrical sources and electrodes. Electrical current is respectively conveyed between active ones of the plurality of electrical sources and active subsets of the plurality of electrodes in accordance with the determined source-electrode coupling configuration. The total number of the electrodes in the active electrode subsets is greater than the total number of the active electrical sources.

2 Claims, 14 Drawing Sheets

NEUROSTIMULATION SYSTEM AND METHOD FOR COMPOUNDING CURRENT TO MINIMIZE CURRENT SOURCES

RELATED APPLICATION

The present application claims the benefit under 35 U.S.C. §119 to U.S. provisional patent application Ser. No. 61/263,652, filed Nov. 23, 2009. The foregoing application is hereby incorporated by reference into the present application in its entirety.

FIELD OF THE INVENTION

The present invention relates to tissue stimulation systems, and more particularly, to a system and method for compounding a discrete number of current sources to controllably generate a spectrum of stimulation currents to be passed to electrodes.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse source (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled electrical energy sources, the distribution of the electrical energy conveyed to or from the electrodes (including the case of the neurostimulator, which may act as an electrode) may be varied such that the electrical energy is supplied via numerous different electrode configurations. In different configurations, the electrodes may provide current or voltage in different relative percentages of positive and negative current or voltage to create different electrical current distributions (i.e., fractionalized electrode configurations).

For example, with reference to FIG. 1, a neurostimulator may have an output current source $1a$ (sometimes referred to as an "anodic current source") and an output current sink $1b$ (sometimes referred to as a "cathodic current source") that are configured to supply/receive stimulating current to/from the electrodes $E_x$, $E_y$, and ultimately to/from tissue (represented by load 5 having a resistance R). The source $1a$ and sink $1b$ are sometimes respectively referred to as PDACs and NDACs, reflecting the fact that the source $1a$ is typically formed of P-type transistors, while the sink $1b$ is typically formed of N-type transistors. The use of transistors of these polarities is sensible given that the source $1a$ is biased to a high voltage (V+), where P-type transistors are most logical, while the sink $1b$ is biased to a low voltage (V−), where N-type transistors are most logical, as shown in FIG. 1. A suitable current source is disclosed in U.S. Pat. No. 6,181,969 ("the '969 patent"), which is expressly incorporated herein by reference in its entirety.

The output current source $1a$ and output current sink $1b$ respectively include current sources $2a$, $2b$ each configured to generate a reference current $I_{ref}$, and digital-to-analog converter (DAC) circuitry $3a$, $3b$ configured for regulating/amplifying the reference current $I_{ref}$ provided by the current sources $2a$, $2b$, and delivering output current $I_{out}$ to the load 5 (having a resistance R). Specifically, the relation between $I_{out}$ and $I_{ref}$ is determined in accordance with input bits arriving on busses $4a$, $4b$, which respectively give the output current source $1a$ and output current sink $1b$ their digital-to-analog functionality. In accordance with the values of the various M bits on busses $4a$, $4b$ any number of output stages (i.e., transistors M1, M2) are tied together in parallel such that $I_{out}$ can range from $I_{ref}$ to $2^{M}*I_{ref}$.

As shown in FIG. 1 for simplicity, the current source $1a$ is coupled to an electrode $E_x$, while the current sink $1b$ is coupled to a different electrode $E_y$. However, each electrode may actually be hard-wired to both the current source $1a$ and the current sink $1b$, only one (or neither) of which is activated at a particular time to allow the electrode to selectively be used as either a source or sink (or as neither).

This architecture is shown in FIG. 2, which shows four exemplary electrodes $E_1$, $E_2$, $E_3$, and $E_4$, each having its own dedicated and hard-wired current source $1a$ and current sink $1b$. Thus, the output current source $1a$ may be associated with electrode $E_2$ (e.g., $E_X$ of FIG. 1) at a particular point in time, while the output current sink $1b$ may be associated with electrode $E_3$ (e.g., $E_Y$ of FIG. 1) at that time. At a later time, electrodes $E_2$ and $E_3$ could be switched, such that $E_2$ now operates as the sink, while electrode $E_3$ operates as the source, or new sources or sinks could be selected, etc.

Another architecture, shown in FIG. 3, uses a plurality of current sources 1 and sinks 2, and further uses a low impedance switching matrix 6 that intervenes between the sources/sinks and the electrodes $E_X$. Each source/sink pair is hard-wired together at common nodes 7, such that the switching matrix 6 intervenes between the nodes 7 and the electrodes. Of course, only one of the source or the sink in each pair is activated at one time, and thus the node 7 in any pair will source or sink current at any particular time. Through appropriate control of the switching matrix 6, any of the nodes 7 may be connected to any of the electrodes $E_X$ at any time. Because all of the available electrodes $E_X$ will typically not be activated at one time, the use of the switching matrix 6 decreases the number of current sources needed to supply the electrical current to the activated electrodes $E_X$. Because a relatively large capacitor is typically associated with each current source/sink, decreasing the number of current sources/sinks in any particular architecture is especially advantageous in that it substantially reduces the space needed in the implantable pulse source.

Further details discussing various architectures of current source/sink circuitry are provided in U.S. Patent Publication No. 2007/0100399, which is expressly incorporated herein by reference.

While the use of switching matrices or networks reduces the number of current sources/sinks needed in order to source/sink electrical current to the desired electrodes, a current source/sink is still utilized for each activated electrode. It is, thus, desirable to minimize the number of current sources/sinks needed, while still providing a requisite spectrum of currents to be distributed to the electrodes.

SUMMARY OF THE INVENTION

In accordance with a first aspect of the present inventions, a neurostimulation system comprises a plurality of electrical terminals configured for being coupled to a respective plurality of electrodes, a plurality of electrical sources (e.g., a current sources, which may be anodic and/or cathodic), and processing circuitry configured for determining a source-electrode coupling configuration from the electrical sources and electrodes. The neurostimulation system further comprises control circuitry configured for respectively conveying electrical current between active ones of the plurality of electrical sources and active subsets of the plurality of electrodes in accordance with the determined source-electrode coupling configuration. The electrical terminals and control circuitry may, e.g., be contained within an implantable device, and the processing circuitry may, e.g., be contained within the implantable device and/or an external programmer.

Any of the active electrical sources may have a fixed absolute output, which may simplify the architecture, or a variable absolute output, which may provide more flexibility in providing current values. At least two of the active electrode sets may be different or may be the same. In one embodiment, at least two of the active electrode subsets include at least one common electrode. In another embodiment, at least two of the active electrode subsets do not include a common electrode. In any event, the total number of the electrodes in the active electrode subsets is greater than the total number of the active electrical sources. As a result, the number of electrical sources (and thus, the number of capacitors that may be associated with the electrical sources) can be decreased relative to the number of electrodes.

In one embodiment, the processor is further configured for selecting electrical current values for the plurality of electrodes, and determining the source-electrode coupling configuration based on the selected electrical current values. For example, the processing circuitry may be configured for determining the source-electrode coupling configuration to best meet the selected electrical current values for the plurality of electrodes. In an optional embodiment, the neurostimulation system further comprises monitoring circuitry configured for measuring impedances adjacent the electrodes, in which case, the processing circuitry may be configured for determining the source-electrode coupling configuration based on the measured impedances. In another optional embodiment, the neurostimulation system further comprises a switching network coupled between the plurality of electrical sources and the plurality of electrical terminals, wherein the control circuitry is configured for operating the switching network to implement the determined source-electrode coupling configuration.

In accordance with a second aspect of the present inventions, a method of providing therapy to a patient implanted with a plurality of electrodes using a plurality of electrical sources (e.g., a current sources, which may be anodic and/or cathodic). The method comprises determining a source-electrode coupling configuration from the electrical sources and electrodes, and respectively conveying electrical current between active ones of the plurality of electrical sources and active subsets of the plurality of electrodes in accordance with the determined source-electrode coupling configuration.

Any of the active electrical sources may have a fixed absolute output, which may simplify the architecture, or a variable absolute output, which may provide more flexibility in providing current values. At least two of the active electrode sets may be different or may be the same. In one method, at least two of the active electrode subsets include at least one common electrode. In another method, at least two of the active electrode subsets do not include a common electrode. In any event, the total number of the electrodes in the active electrode subsets is greater than the total number of the active electrical sources. As a result, the number of electrical sources (and thus, the number of capacitors that may be associated with the electrical sources) can be decreased relative to the number of electrodes.

One method further comprises selecting electrical current values for the plurality of electrodes, and determining the source-electrode coupling configuration based on the selected electrical current values. For example, the source-electrode coupling configuration may be determined to best meet the selected electrical current values for the plurality of electrodes. Another method further comprises measuring impedances adjacent the electrodes, in which case, the source-electrode coupling configuration may be determined based on the measured impedances.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
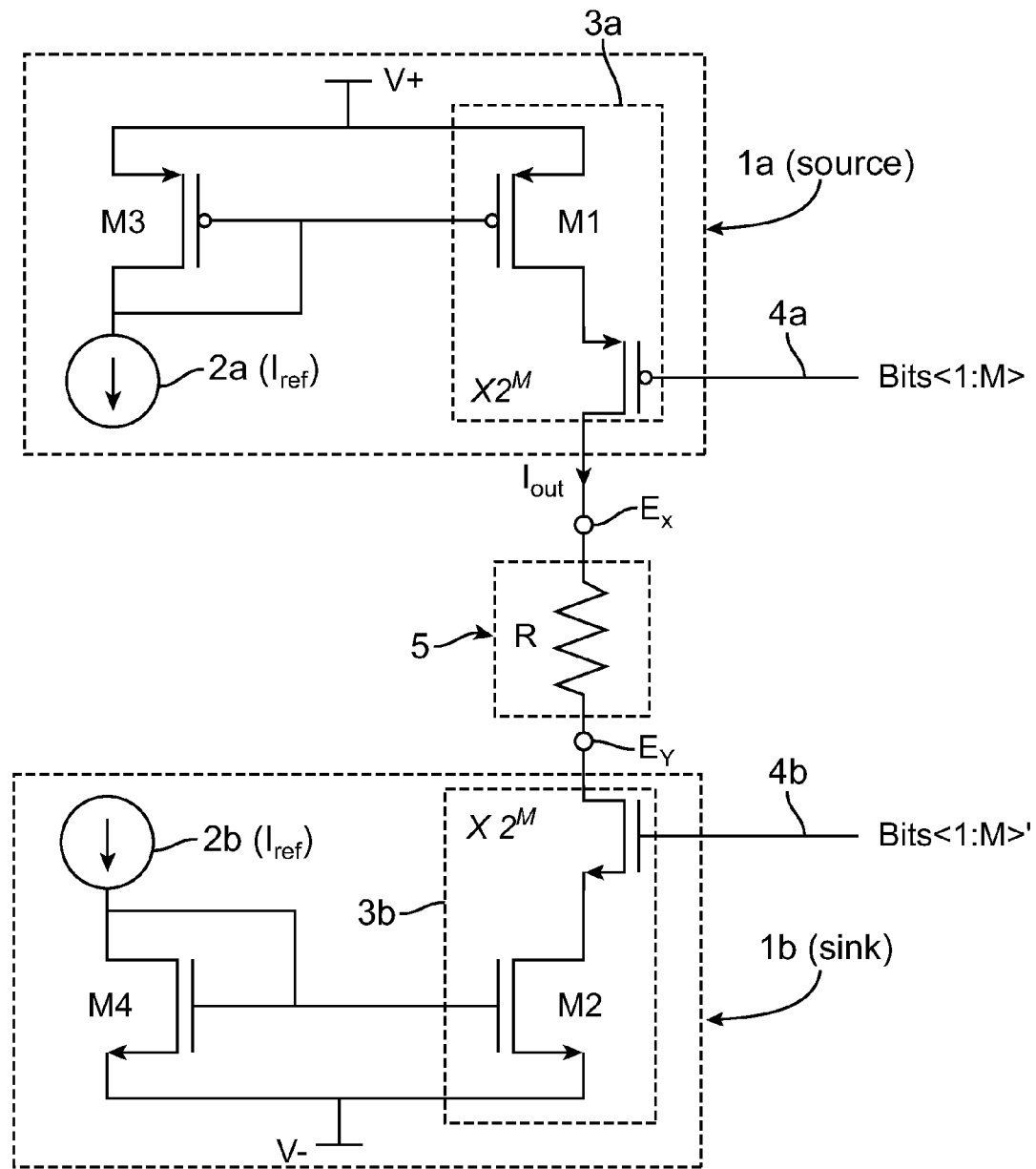
FIG. 1 is circuit diagram of a prior art embodiment of current source/current sink circuitry.
Figure 2:
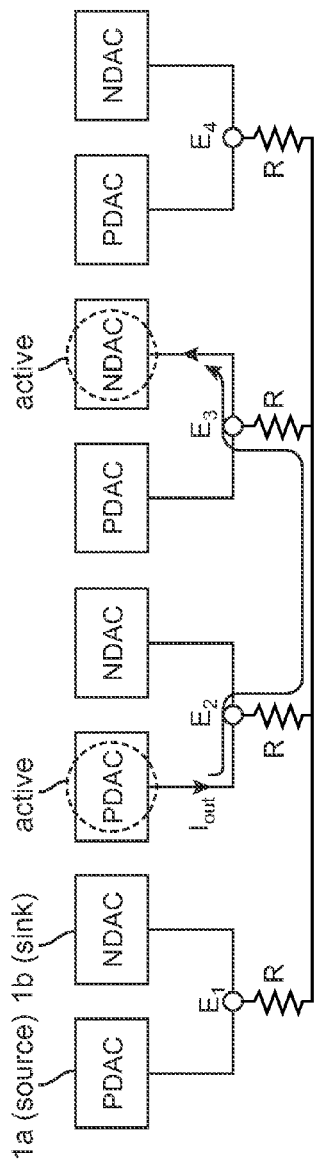
FIG. 2 is a block diagram of a prior art architecture for coupling output current sources and current sinks to a plurality of electrodes.
Figure 3:
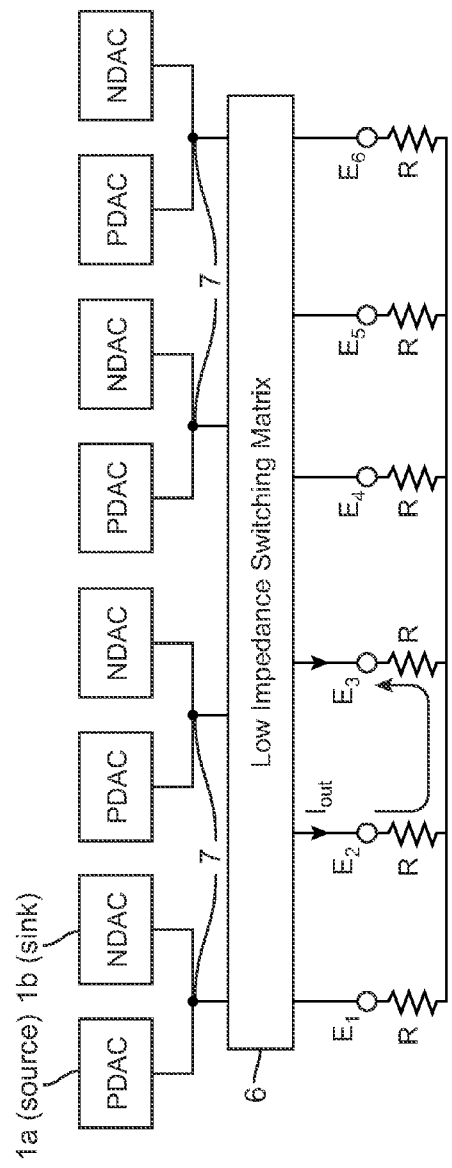
FIG. 3 is a block diagram of another prior art architecture for coupling output current sources and current sinks to a plurality of electrodes.
Figure 4:
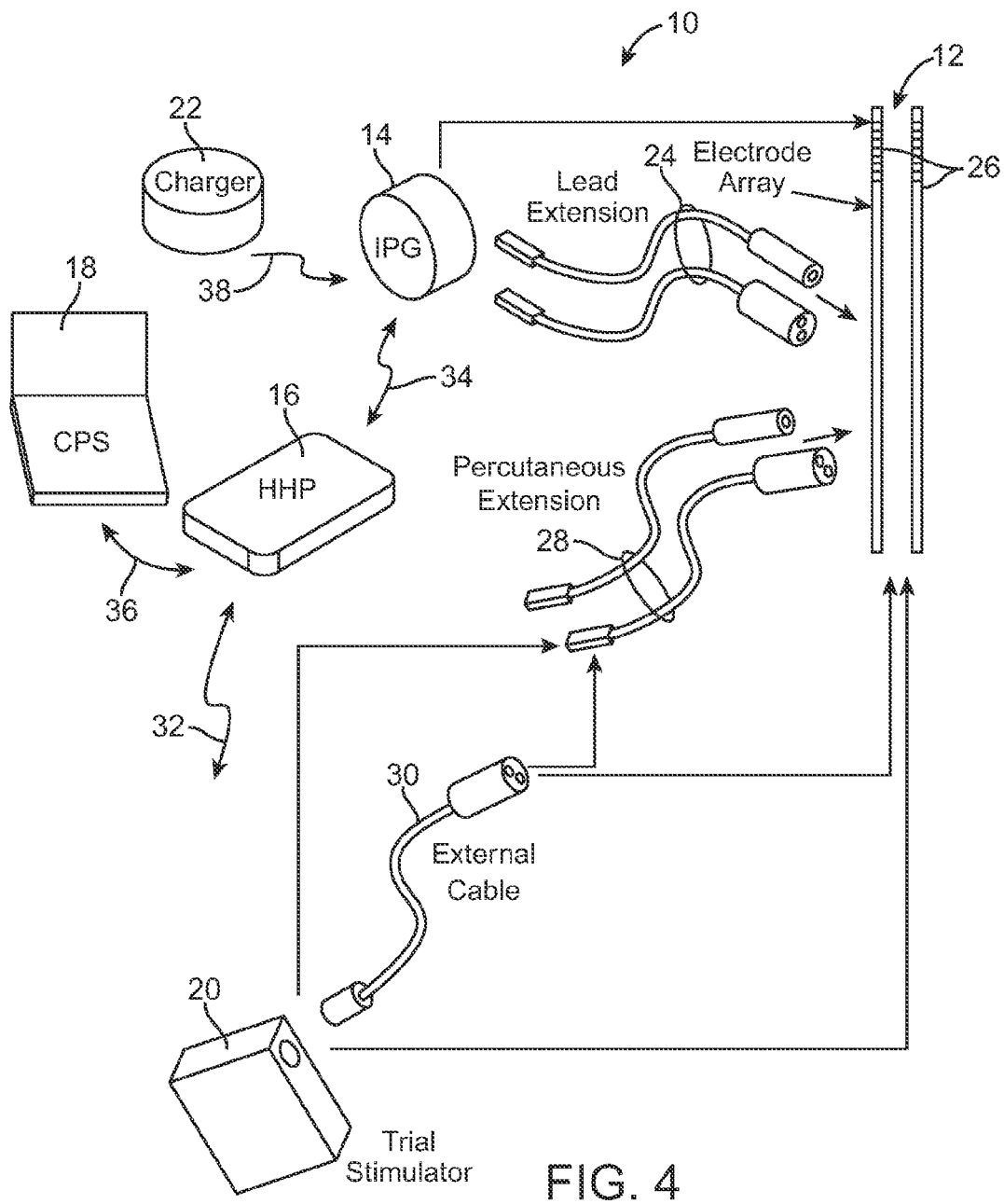
FIG. 4 is a plan view of an embodiment of a spinal cord stimulation (SCS) system arranged in accordance with the present inventions.

Turning first to FIG. 4, an exemplary SCS system 10 generally includes one or more (in this case, two) implantable stimulation leads 12, an implantable pulse source (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 5:
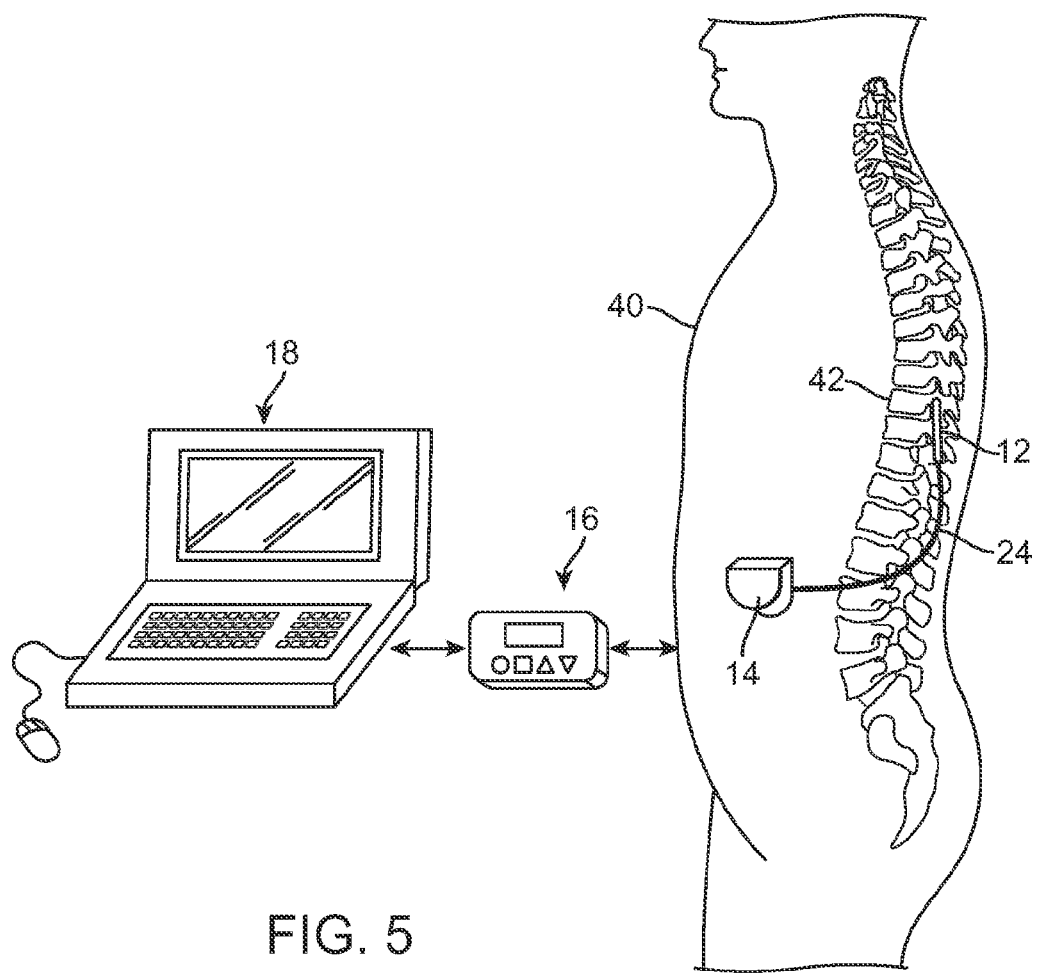
FIG. 5 is a plan view of the SCS system of FIG. 4 in use with a patient.

As shown in FIG. 5, the electrode leads 12 are implanted within the spinal column 42 of a patient 40. The preferred placement of the stimulation leads 12 is adjacent, i.e., resting near, or upon the dura, adjacent to the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 6:
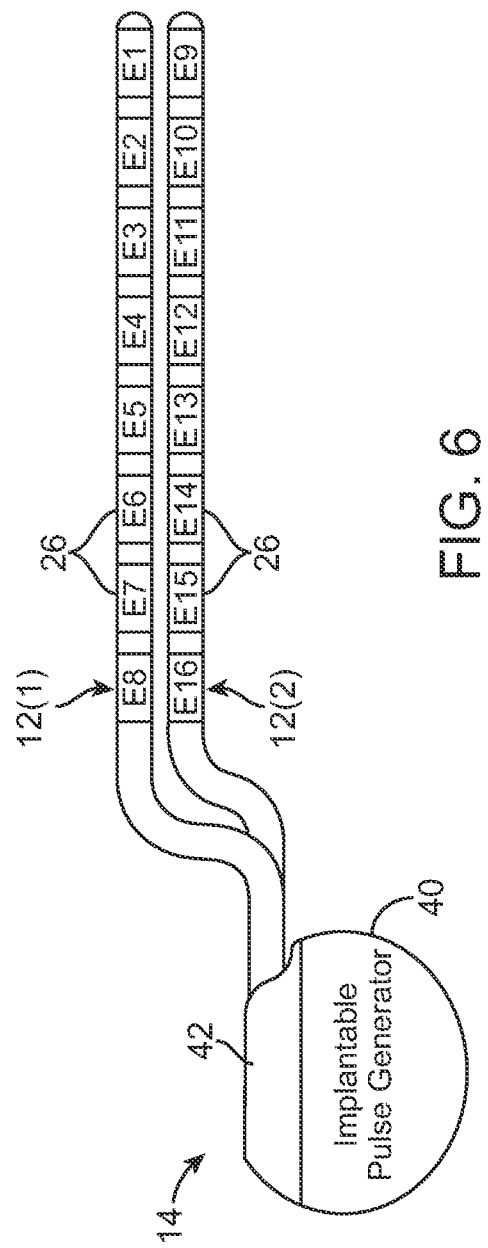
FIG. 6 is a profile view of an implantable pulse source (IPG) used in the SCS system of FIG. 4.

Referring now to FIG. 6, the external features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12(1) and 12(2) mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 7:
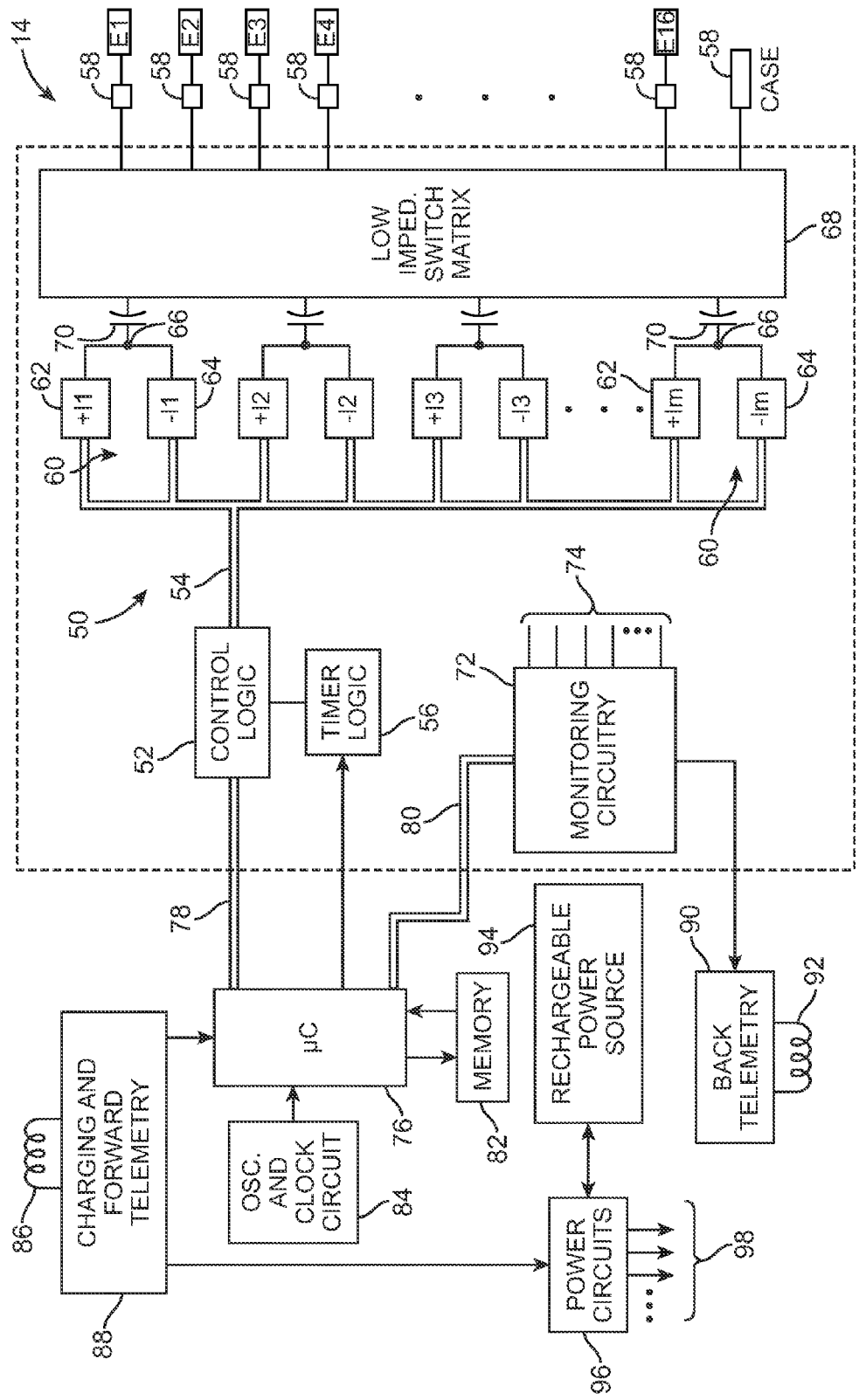
FIG. 7 is a block diagram of the internal components of the IPG of FIG. 6.

Turning next to FIG. 7, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, and pulse shape under control of control logic 52 over data bus 54. Control of the pulse rate and pulse width of the electrical waveform is facilitated by timer logic circuitry 56, which may have a suitable resolution, e.g., 10 μs. The stimulation energy generated by the stimulation output circuitry 50 is output to electrical terminals 58 corresponding to electrodes E1-E16.

The analog output circuitry 50 may either comprise one or more independently controlled electrical sources, which take the form of current sources and/or current sinks, for providing stimulation pulses of a specified and known amperage to or from the electrodes 26, or voltage sources and/or voltage sinks for providing stimulation pulses of a specified and known voltage at the electrodes 26.

For example, in the illustrated embodiment, the stimulation output circuitry 50 comprises a plurality m independent current source pairs 60 capable of supplying stimulation energy to the electrical terminals 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66.

Figure 8:
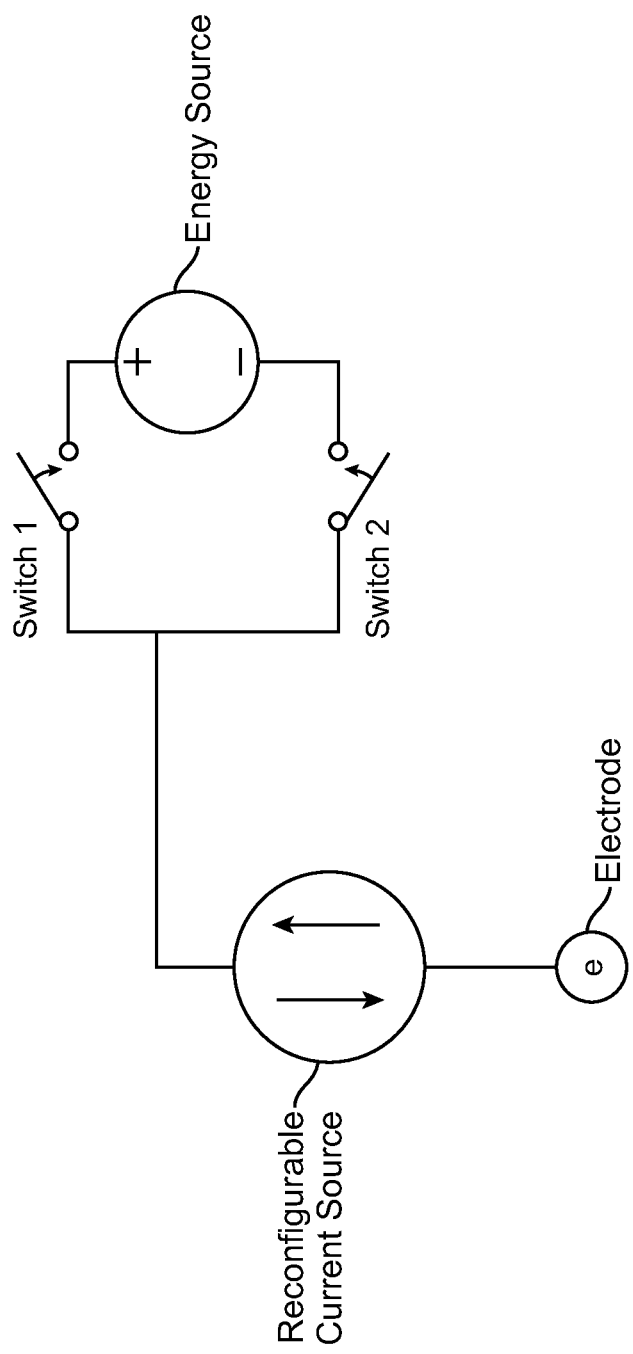
FIG. 8 is a circuit diagram of a reconfigurable current source that can be used in the IPG of FIG. 7.

In essence, each current source pair 60 takes the form of a reconfigurable current source whose polarity can be switched. That is, by activating the anodic current source 62 and deactivating the cathodic current source 64, the current source pair 60 can be configured as an anodic current source, and by deactivating the anodic current source 62 and activating the cathodic current source 64, the current source pair 60 can be configured as a cathodic current source. Alternatively, instead of a having current sources pairs 60, each of which includes an anodic current source and a cathodic current source, the reconfigurable current source can have a current source that can be switched between the positive terminal and the positive terminal of an energy source to selectively reconfigure the current source between an anodic current source and a cathodic current source. For example, as illustrated in FIG. 8, the reconfigurable current source is coupled between an electrode and an energy source. Switches 1 and 2 are coupled between the respective positive and negative terminals of the energy source and the side of the current source opposite to the electrode. When the switch 1 is closed and the switch 2 is opened, the current source is coupled to the positive terminal of the energy source, thereby being configured as an anodic current source. In contrast, when the switch 1 is opened and the switch 2 is closed, the current source is coupled to the negative terminal of the energy source, thereby being configured as a cathodic current source.

Referring back to FIG. 7, the stimulation output circuitry 50 further comprises a low impedance switching matrix 68 through which the common node 66 of each current source pair 60 is connected to any of the electrical terminals 58, and a capacitor 70 coupled between the common node 66 of each current source pair 60 and the switching matrix 68. Significantly, as will be discussed in further detail below, the switching matrix 68 may be used to form source/electrode couplings (i.e., which active current sources 64 and active electrode(s) 26 are to be coupled together) that include more activated electrodes than activated current sources, thereby minimizing the number of current sources needed. As will also be discussed in further detail below, the current sources 64 may have a fixed absolute magnitude value or may have a variable absolute magnitude value, and preferably have different magnitude values or ranges relative to each other in order to increase the variability of the source/electrode couplings.

Hence, it is seen that each of the programmable electrical terminals 58 can be programmed to have a positive (sourcing current), a negative (sinking current), or off (no current) polarity. Further, the amplitude of the current pulse being sourced or sunk to or from a given electrode may be programmed to one of several discrete current levels, e.g., between 0 to 10 mA in steps of 100 µA, within the output voltage/current requirements of the IPG 14. Additionally, in one embodiment, the total current output by a group of electrical terminals 58 can be up to ±20 mA (distributed among the electrodes included in the group). Also, the pulse width of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 1000 pulses per second (pps). Other programmable features can include slow start/end ramping, burst stimulation cycling (on for X time, off for Y time), interphase (i.e., the duration between first and second phases of biphasic energy), and open or closed loop sensing modes. Moreover, it is seen that each of the electrical terminals 58 can operate in a multipolar mode, e.g., where two or more electrical terminals are grouped to source/sink current at the same time. Alternatively, each of the electrical terminals 58 can operate in a monopolar mode where, e.g., the electrical terminals 58 are configured as cathodes (negative), and case of the IPG 14 is configured as an anode (positive).

It can be appreciated that an electrical terminal 58 may be assigned an amplitude and included with any of up to k possible groups, where k is an integer corresponding to the number of channels, and in one embodiment, is equal to 4, and with each channel k having a defined pulse amplitude, pulse width, pulse rate, and pulse shape. Other channels may be realized in a similar manner. Thus, each channel identifies which electrical terminals 58 (and thus electrodes) are selected to synchronously source or sink current, the pulse amplitude at each of these electrical terminals, and the pulse width, pulse rate, and pulse shape. Amplitudes and polarities of electrodes on a channel may vary, e.g., as controlled by the RC 16. External programming software in the CP 18 is typically used to set stimulation parameters including electrode polarity, amplitude, pulse rate and pulse width for the electrodes of a given channel, among other possible programmable features. The operation of this output stimulation circuitry, including alternative embodiments of suitable output circuitry for performing the same function of generating stimulation pulses of a prescribed amplitude and width, is described more fully in U.S. Pat. Nos. 6,516,227 and 6,993, 384, which are expressly incorporated herein by reference.

It should be appreciated that, although the embodiment described in reference to FIG. 7 uses current sources, alternative embodiments may utilize voltage sources. In such cases, current generated by a given voltage source may be maintained at a constant defined current utilizing techniques such as those described in U.S. Provisional Patent Application Ser. No. 61/083,491, entitled "System and Method for Maintaining a Distribution of Currents in an Electrode Array Using Independent Voltage Sources," which is expressly incorporated herein by reference. The currents pertinent to several voltage sources may be combined with a switch in a similar manner as described herein in reference to combined current sources.

The IPG 14 further comprises monitoring circuitry 72 for monitoring the status of various nodes or other points 74 throughout the IPG 14, e.g., power supply voltages, temperature, battery voltage, and the like. Notably, the electrodes 26 fit snugly within the epidural space of the spinal column, and because the tissue is conductive, electrical measurements can be taken between the electrodes 26. Thus, the monitoring circuitry 72 is configured for taking such electrical measurements (e.g., current output magnitude, electrode impedance, field potential, evoked action potentials, etc.) for performing such functions as detecting fault conditions between the electrodes 26 and the analog output circuitry 50, determining the coupling efficiency between the electrodes 26 and the tissue, facilitating lead migration detection, etc. In the case where voltage sources (instead of current sources) are used, the monitoring circuitry 72 can measure the impedances on the electrodes 26 in order to maintain a desired current distribution on the active electrodes 26 by adjusting the voltages on the active electrodes 26. Furthermore, whether current sources or voltage sources are used, the monitoring circuitry 72 will be used to measure impedances for ensuring that the actual current values best match the desired current values on the electrodes, as will be discussed in further detail below.

Electrical parameter data can be measured using any one of a variety means. For example, the electrical parameter data measurements can be made on a sampled basis during a portion of the time while the electrical stimulus pulse is being applied to the tissue (e.g., if the required voltage distribution necessary to achieve the desired current distribution is to be estimated at a non-zero operating point of the stimulation), as described in U.S. Pat. No. 7,317,948, which is expressly incorporated herein by reference. Alternatively, the electrical parameter data measurements can be made independently of the electrical stimulation pulses (e.g., if the required voltage distribution necessary to achieve the desired current distribution is to be estimated at a zero operating point of the stimulation), such as described in U.S. Pat. Nos. 6,516,227 and 6,993,384, which are expressly incorporated herein by reference.

Further details discussing the measurement of electrical parameter data, such as electrode impedance, field potential, and evoked action potentials, as well as physiological parameter data, such as pressure, translucence, reflectance and pH (which can alternatively be used) are set forth in U.S. patent application Ser. No. 10/364,436, entitled "Neural Stimulation System Providing Auto Adjustment of Stimulus Output as a Function of Sensed Impedance," U.S. patent application Ser. No. 10/364,434, entitled "Neural Stimulation System Providing Auto Adjustment of Stimulus Output as a Function of Sensed Pressure Changes," and U.S. patent application Ser. No. 11/096,483, entitled "Apparatus and Methods for Detecting Migration of Neurostimulation Leads," which are expressly incorporated herein by reference.

The IPG 14 further comprises processing circuitry in the form of a microcontroller (µC) 76 that controls the control logic over data bus 78, and obtains status data from the monitoring circuitry 72 via data bus 80. The IPG 14 additionally controls the timer logic 56 and switching matrix 68.

The IPG 14 further comprises memory 82 and oscillator and clock circuitry 84 coupled to the microcontroller 76. The microcontroller 76, in combination with the memory 82 and oscillator and clock circuit 84, thus comprise a microprocessor system that carries out a program function in accordance with a suitable program stored in the memory 82. Alternatively, for some applications, the function provided by the microprocessor system may be carried out by a suitable state machine.

Thus, the microcontroller 76 generates the necessary control and status signals, which allow the microcontroller 76 to control the operation of the IPG 14 in accordance with a selected operating program and stimulation parameters. In controlling the operation of the IPG 14, the microcontroller 76 is able to individually generate a train of stimulus pulses at the electrodes 26 using the analog output circuitry 50, in combination with the control logic 52 and timer logic 56, thereby activating selected ones of the electrodes 26, including the monopolar case electrode. In accordance with stimulation parameters stored within the memory 82, the microcontroller 76 may control the polarity, amplitude, rate, pulse width and channel through which the current stimulus pulses are provided. The microcontroller 76 also facilitates the storage of electrical parameter data (or other parameter data) measured by the monitoring circuitry 72 within memory 82, and also provides any computational capability needed to analyze the raw electrical parameter data obtained from the monitoring circuitry 72 and compute numerical values from such raw electrical parameter data.

The IPG 14 further comprises an alternating current (AC) receiving coil 86 for receiving programming data (e.g., the operating program and/or stimulation parameters) from the RC 16 and/or CP 18 (shown in FIG. 5) in an appropriate modulated carrier signal, and charging and forward telemetry circuitry 88 for demodulating the carrier signal it receives through the AC receiving coil 86 to recover the programming data, which programming data is then stored within the memory 82, or within other memory elements (not shown) distributed throughout the IPG 14.

The IPG 14 further comprises back telemetry circuitry 90 and an alternating current (AC) transmission coil 92 for sending informational data sensed through the monitoring circuitry 72 to the RC 16 and/or CP 18 (shown in FIG. 5). The back telemetry features of the IPG 14 also allow its status to be checked. For example, when the RC 16 and/or CP 18 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18. The back telemetry features allow raw or processed electrical parameter data (or other parameter data) previously stored in the memory 82 to be downloaded from the IPG 14 to the RC 16 and/or CP 18.

The IPG 14 further comprises a rechargeable power source 94 and power circuits 96 for providing the operating power to the IPG 14. The rechargeable power source 94 may, e.g., comprise a lithium-ion or lithium-ion polymer battery. The rechargeable battery 94 provides an unregulated voltage to the power circuits 96. The power circuits 96, in turn, generate the various voltages 98, some of which are regulated and some of which are not, as needed by the various circuits located within the IPG 14. The rechargeable power source 94 is recharged using rectified AC power (or DC power converted from AC power through other means, e.g., efficient AC-to-DC converter circuits, also known as "inverter circuits") received by the AC receiving coil 86. To recharge the power source 94, the external charger 22 (shown in FIG. 4), which generates the AC magnetic field, is placed against, or otherwise adjacent, to the patient's skin over the implanted IPG 14. The AC magnetic field emitted by the external charger induces AC currents in the AC receiving coil 86. The charging and forward telemetry circuitry 88 rectifies the AC current to produce DC current, which is used to charge the power source 94. While the AC receiving coil 86 is described as being used for both wirelessly receiving communications (e.g., programming and control data) and charging energy from the external device, it should be appreciated that the AC receiving coil 86 can be arranged as a dedicated charging coil, while another coil can be used for bi-directional telemetry.

It should be noted that the diagram of FIG. 7 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Source," which are expressly incorporated herein by reference. It should be noted that rather than an IPG, the SCS system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, the switching matrix 68 may be used to form source/electrode couplings in a manner that minimizes the number of current sources needed. In particular, processing circuitry (such as the microcontroller 76 contained in the IPG 14, or alternatively, processing circuitry (not shown) contained within the RC 16 or CP 18) determines a source-electrode coupling configuration from the available current sources 64 and electrodes 26. Such processing circuitry may also select the electrical current values for the electrodes 26 (e.g., in response to programming functions performed at the RC 16 or CP 18), in which case, the source-electrode coupling configuration can be based on the selected electrical current values. For example, the processing circuitry can determine the source-electrode coupling configuration that best meets the selected electrical current values for the electrodes 26, as will be discussed in further detail below.

Once the source-electrode coupling configuration is determined, the control circuitry (including control logic 52 and timer logic 56), as configured by the microcontroller 76, conveys electrical current between active ones of the current sources 64 and active subsets (either one or a plurality) of the electrodes 26 in accordance with the determined source-electrode coupling configuration, such that the total number of electrodes 26 in the active electrode subsets is greater than the total number of the active current sources 64. In essence, because the microcontroller 76 may determine the source-electrode coupling configuration in a manner that best matches the selected electrical current values, any requirement that the current sources independently convey electrical current to or from the electrodes (i.e., one-to-one correspondence between the current sources and electrodes) is obviated, and as such, the number of current sources 64 required to drive any particular combination of electrodes 26 may be decreased.

Before discussing the details of how the source-electrode coupling configuration is determined to minimize the number of activated sources required to drive the active electrodes, it will be first worthwhile to discuss how the outputs of the current sources can be combined to generate a variety of currents that will be assumed when determining the source-electrode couplings.

Figure 9:
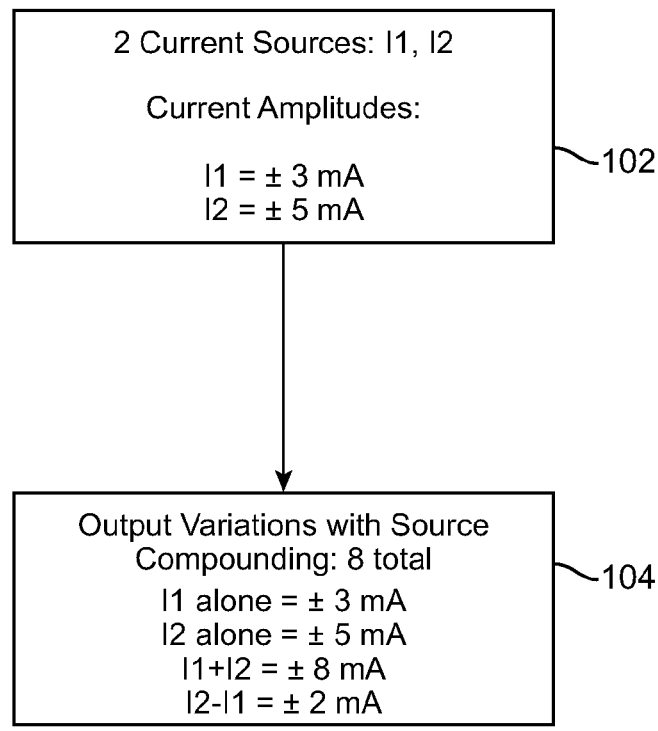
FIG. 9 illustrates an example scenario of one embodiment wherein two current sources in the IPG of FIG. 6 may be combined to make four output variations possible.
Figure 10:
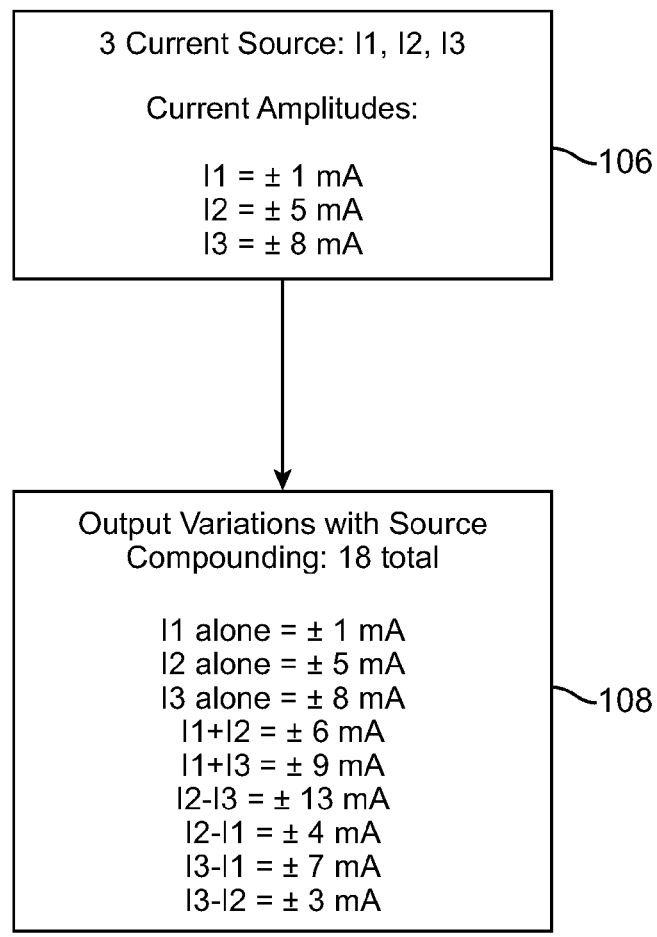
FIG. 10 illustrates an example scenario of one embodiment wherein three current sources in the IPG of FIG. 6 may be combined to make nine output variations possible.

As a general rule, from a total number of N current sources, the output of two active sources can be compounded to create a total of $2 \times N^2$ different outputs. For example, referring to FIG. 9, given two (N) different current sources (I1 and I2), each having a different current amplitude 102 (±3 mA and ±5 mA), the current sources can be utilized alone, added together, or subtracted from each other to provide a total of four ($N^2$) absolute current amplitudes 104 (2 mA, 3 mA, 5 mA, and 8 mA). Assuming that the current values can be both negative and positive, a total ($2 \times N^2$) of eight current amplitudes (±2 mA, ±3 mA, ±5 mA, and ±8 mA) can be provided. Similarly, referring to FIG. 10, given three (N) different current sources (I1, I2, and I3), each having a different amplitude 106 (±1 mA, ±3 mA, and ±8 mA), the current sources can be utilized alone, added together, or subtracted from each other to provide a total ($N^2$) of nine different absolute current amplitudes 108 (1 mA, 3 mA, 4 mA, 5 mA, 6 mA, 7 mA, 8 mA, 9 mA, and 13 mA). Assuming that the absolute current values can be both negative and positive, a total ($2 \times N^2$) of eighteen current amplitudes (±1 mA, ±3 mA, ±4 mA, ±5 mA, ±6 mA, ±7 mA, ±8 mA, ±9 mA, and ±13 mA) can be provided. Each of the current sources can be reconfigurable between positive and negative polarities, such that they can be combined in an additive manner or a subtractive manner to produce the desired combined current.

It should be appreciated that although the examples in FIGS. 9 and 10 illustrate the number of different outputs that can be provided by compounding two current sources at a time, more than two current sources can be compounded to provide even more current amplitudes. It should also be appreciated that, to the extent that current source pairs (an anodic source and a cathodic source) are used to implement both an adding function (use anodic source to add current) and a subtracting function (use cathodic source to subtract current), a theoretical total of N current sources will actually be 2*N current sources. However, as will be discussed in further detail below, the total number of active current sources may be less than the total number of active electrodes.

Notably, the many different current values provided by compounding current sources can be applied to active electrodes in a variety of manners to provide many more current values on the electrodes themselves. This can be accomplished by defining different source-electrode couplings, and conveying electrical current between active ones of the current sources and active subsets of the electrodes 26 in accordance with the determined source-electrode couplings, as briefly discussed above.

For example, with reference to FIGS. 11*a-g*, various source-electrode coupling configurations are shown as being defined for two current sources (S1, S2), and three electrodes (e1, e2, e3), with the first source S1 having a nominal current output of 3 mA, and the second source S2 having a nominal current output of 5 mA. The two current sources S1, S2 may be arbitrarily assigned to any two of the reconfigurable current sources illustrated in FIG. 7, and the three electrodes e1, e2, e3 are capable of being arbitrarily assigned to any three of the sixteen electrodes E1-E16 and case electrode illustrated in FIG. 7. The different source-electrode coupling configurations can be made with an intervening switch, such as the switching matrix 62 shown in FIG. 7.

Figure 11A:
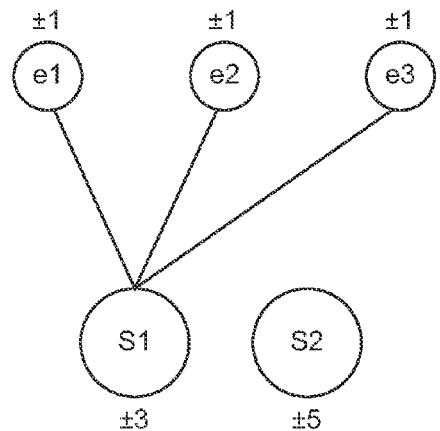
FIGS. 11a-11g illustrate different source-electrode coupling configurations that can be implemented by the IPG of FIG. 6 using two fixed amplitude current sources and three electrodes.
Figure 11B:
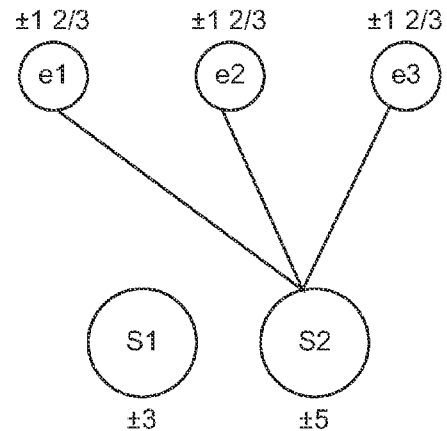

In the first source-electrode coupling configuration, the first source S1 is coupled to all three electrodes e1, e2, e3, and the second source S2 is not coupled to any of the electrodes e1, e2, e3, resulting in a current value of 1 mA for each of the electrodes e1, e2, e3 (if the source S1 is anodic) or a current value of −1 mA for each of the electrodes e1, e2, e3 (if source S1 is anodic) (FIG. 11*a*). In the second source-electrode coupling configuration, the first source S1 is not coupled to any of the electrodes e1, e2, e3, and the second source S2 is coupled to all three of the electrodes e1, e2, e3, resulting in a current value of 1⅔ mA for each of the electrodes e1, e2, e3 (if the source S2 is anodic) or a current value of −1⅔ mA for each of the electrodes e1, e2, e3 (if the source S2 is cathodic) (FIG. 11*b*).

Figure 11C:
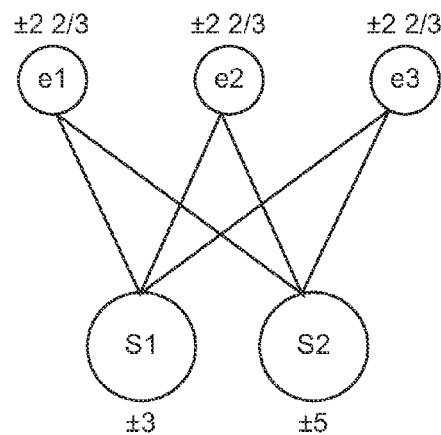
Figure 11D:
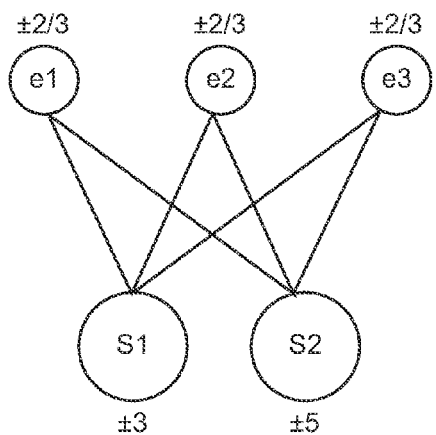

In the third source-electrode coupling configuration, the first source S1 is coupled to all three of the electrodes e1, e2, e3, and the second source S2 is coupled to all three of the electrodes e1, e2, e3, resulting in a current value of 2⅔ mA for each of the electrodes e1, e2, e3 (if both the sources S1, S2 are anodic) or a current value of −2⅔ mA for each of the electrodes e1, e2, e3 (if both the sources S1, S2 are cathodic) (FIG. 11*c*). In the fourth source-electrode coupling configuration, the first source S1 is coupled to all three of the electrodes e1, e2, e3, and the second source S1 is coupled to all three electrodes e1, e2, e3, resulting in a current value of ⅔ mA for each of the electrodes e1, e2, e3 (if the source S1 is cathodic, and the source S2 is anodic) or a current value of −⅔ mA for each of the electrodes e1, e2, e3 (if the source S1 is anodic, and the source S2 is cathodic) (FIG. 11*d*).

Figures 11E, 11F:
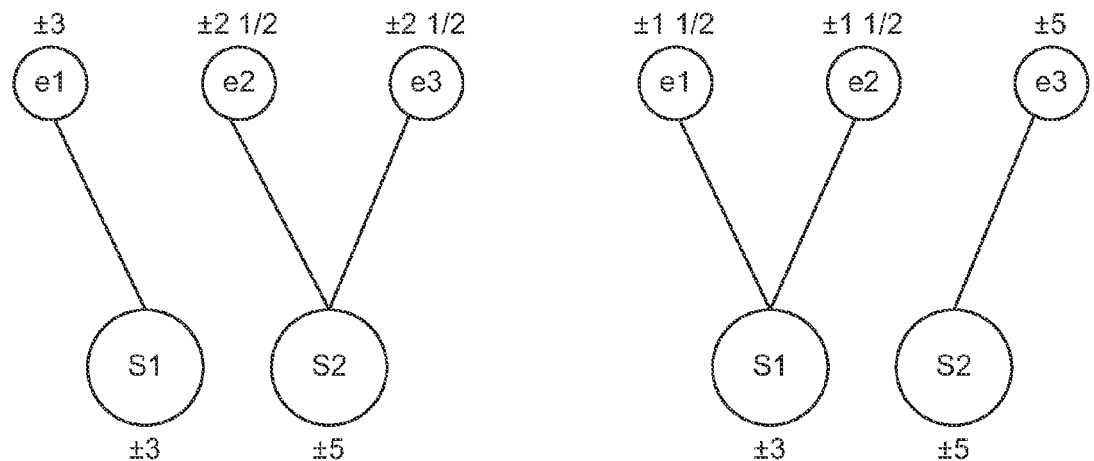

In the fifth source-electrode coupling configuration, the first source S1 is coupled to the first electrode e1, and the second source S2 is coupled to the second and third electrodes e2, e3, resulting in a current value of 3 mA for the electrode e1 and 2½ mA for each of the electrodes e2, e3 (if the source S1 is cathodic, and the source S2 is anodic) or a current value of −3 mA for the electrode e1, and −2½ mA for each of the electrodes e2, e3 (if the source S1 is anodic, and the source S2 is cathodic) (FIG. 11*e*). In the sixth source-electrode coupling configuration, the first source S1 is coupled to the first and second electrodes e1, e2, and the second source S2 is coupled to the third electrode e3, resulting in a current value of 1½ mA for each of the electrodes e1, e2 and 5 mA for electrode e3 (if the source S1 is cathodic, and the source S2 is anodic) or a current value of −1½ mA for each of the electrodes e1, e2, and −5 mA for the electrode e3 (if the source S1 is anodic, and the source S2 is cathodic) (FIG. 11*f*).

Figure 11G:
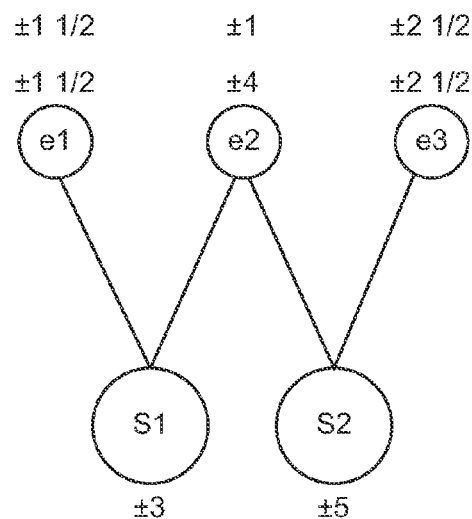

In the seventh source-electrode coupling configuration, the first source S1 is coupled to the first and second electrodes e1, e2, and the second source S2 is coupled to the second and third electrodes e2, e3, resulting in a current value of 1½ mA for the electrode e1, 4 mA for the electrode e2, and 2½ mA for the electrode e3 (if both the sources S1 and S2 are anodic), or a current value of −1½ mA for the electrode e1, −4 mA for the electrode e2, and −2½ mA for the electrode e3 (if both the sources S1 and S2 are cathodic), or a current value of −1½®mA for the electrode e1, 1 mA for the electrode e2, and 2½ mA for the electrode e3 (if the source S1 is cathodic, and the source S2 is anodic), or a current value of 1½ mA for the electrode e1, −1 mA for the electrode e2, and −2½ mA for the electrode e3 (if the source S1 is anodic, and the source S2 is cathodic) (FIG. 11g).

It should be noted that the active electrode subsets associated with the respective sources may have at least one common electrode. For example, in the third and fourth source-electrode coupling configurations illustrated in FIGS. 11c and 11d, the electrode subsets respectively coupled to the first and second sources S1, S2 include all three electrodes e1, e2, e3, and in the seventh source-electrode coupling configuration illustrated in FIG. 11g, the electrode subsets coupled to the first and second sources S1, S2 include the second electrode e2. Or, the active electrode subsets associated with the respective source may not have a common electrode. For example, in the fifth source-electrode coupling configuration illustrated in FIG. 11e, the electrode subset coupled to the first source S1 includes the electrode e1, whereas the electrode subset coupled to the second source S2 includes the electrodes e2, e3, and in the sixth source-electrode coupling configuration illustrated in FIG. 11f, the electrode subset coupled to the first source S1 includes the electrodes e1, e2, whereas the electrode subset coupled to the second source S2 includes the electrode e3.

It should also be noted that the active electrode subsets associated with the respective sources can be different from each other. For example, in the fifth source-electrode coupling configuration illustrated in FIG. 11e, the electrode coupling subset coupled to the first source S1 includes the electrode e1, whereas the electrode subset coupled to the second source S2 includes the electrodes e2, e3. In the sixth source-electrode coupling configuration illustrated in FIG. 11f, the electrode coupling subset coupled to the first source S1 includes the electrodes e1, e2, whereas the electrode subset coupled to the second source S2 includes the electrode e3. In the seventh source-electrode coupling configuration illustrated in FIG. 11g, the electrode coupling subset coupled to the first source S1 includes the electrodes e1, e2, whereas the electrode subset coupled to the second source S2 includes the electrodes e2, e3. Or, the active electrode subsets associated with the respective sources can be the same as each other. For example, in the third and fourth source-electrode coupling configurations illustrated in FIGS. 11c and 11d, the electrode subsets respectively coupled to the first and second sources S1, S2 include all three electrodes e1, e2, e3.

Although the current sources illustrated in FIGS. 11a-11g are described as having fixed magnitudes, it should be noted that one or more of these sources can have a variable magnitude, such that the current values on the electrodes e1, e2, e3 can be better controlled. For example, the current magnitude of each of the sources S1, S2 may be varied by ±1 mA, providing a relatively large current variability on the electrodes e1, e2, e3, as illustrated in FIGS. 12a-12g.

Figures 12A, 12B:
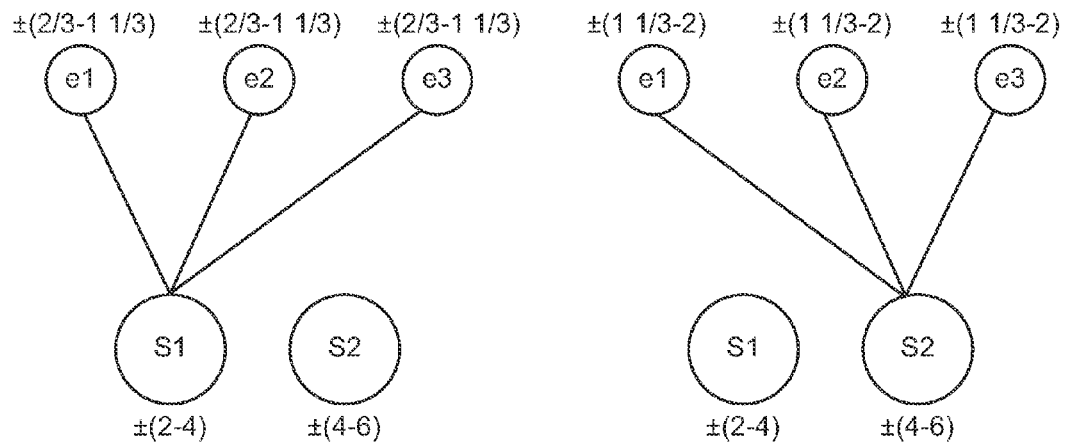
FIGS. 12a-12g illustrate different source-electrode coupling configurations that can be implemented by the IPG of FIG. 6 using two variable amplitude current sources and three electrodes.
Figures 12C, 12D:
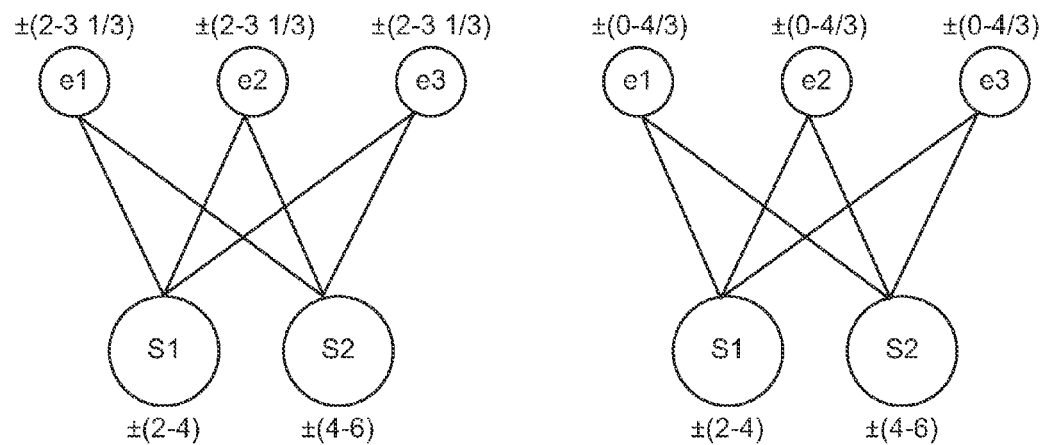
Figures 12E, 12F:
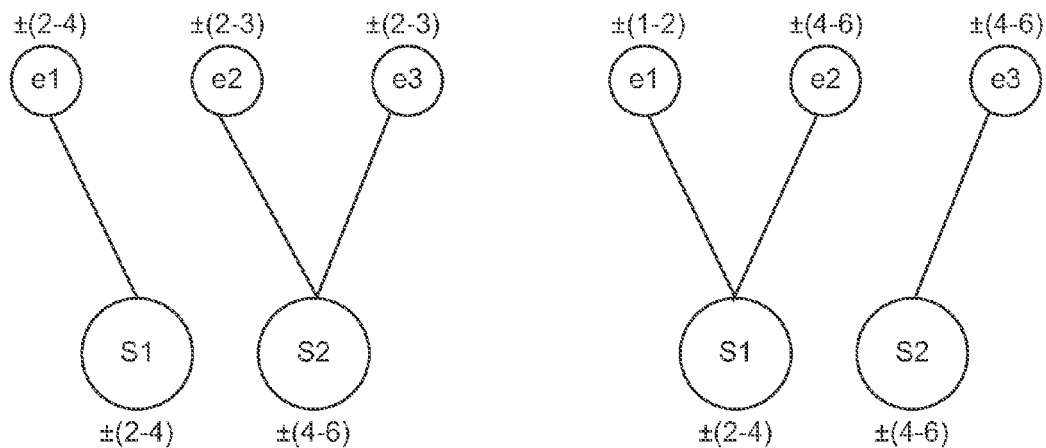
Figure 12G:
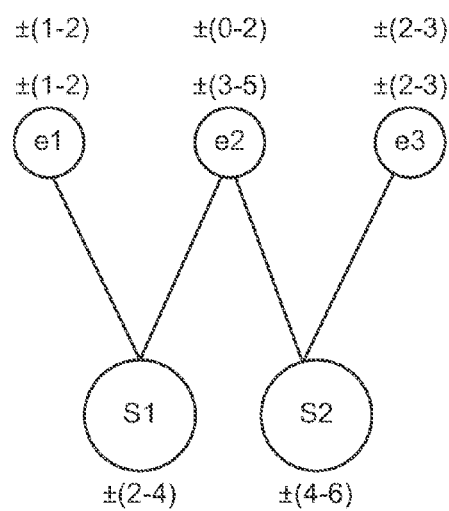

For example, the first source-electrode coupling configuration may result in a current range of ⅔ to 1⅓ mA for each of the electrodes e1, e2, e3 (if both the sources S1, S2 are anodic) or a current range of −⅔ to 1⅓ for each of the electrodes e1, e2, e3 (if both the sources S1, S2 are anodic) (FIG. 12a). The second source-electrode coupling configuration may result in a current range of 1⅓ to 2 mA for each of the electrodes e1, e2, e3 (if both the sources S1, S2 are anodic) or a current range of −1⅓ to −2 mA for each of the electrodes e1, e2, e3 (if both the sources S1, S2 are cathodic) (FIG. 12b). The third source-electrode coupling configuration may result in a current range of 2 to 3⅓ mA for each of the electrodes e1, e2, e3 (if both the sources S1, S2 are anodic) or a current range of −2 to −3⅓ mA for each of the electrodes e1, e2, e3 (if both the sources S1, S2 are cathodic) (FIG. 12c). The fourth source-electrode coupling configuration may result in a current range of 0 to ⅘ mA for each of the electrodes e1, e2, e3 (if the source S1 is cathodic, and the source S2 is anodic) or a current range of 0 to −⅘ mA for each of the electrodes e1, e2, e3 (if the source S1 is anodic, and the source S2 is cathodic) (FIG. 12d). The fifth source-electrode coupling configuration may result in a current range of 2 to 4 mA for the electrode e1 and 2 to 3 mA for each of the electrodes e2, e3 (if the source S1 is cathodic, and the source S2 is anodic) or a current range of −2 to −4 mA for the electrode e1, and −2 to −3 mA for each of the electrodes e2, e3 (if the source S1 is anodic, and the source S2 is cathodic) (FIG. 12e). The sixth source-electrode coupling configuration results in a current range of 1 to 2 mA for each of the electrodes e1, e2 and 4 to 6 mA for electrode e3 (if the source S1 is cathodic, and the source S2 is anodic) or a current range of −2 to −1 mA for each of the electrodes e1, e2, and −4 to −6 mA for the electrode e3 (if the source S1 is anodic, and the source S2 is cathodic) (FIG. 12f). The seventh source-electrode coupling configuration may result in a current range of 1 to 2 mA for the electrode e1, 3 to 5 mA for the electrode e2, and 2 to 3 mA for the electrode e3 (if both the sources S1 and S2 are anodic), or a current range of −1 to −2 mA for the electrode e1, −3 to −5 mA for the electrode e2, and −2 to −3 mA for the electrode e3 (if both the sources S1 and S2 are cathodic), or a current range of −1 to −2 mA for the electrode e1, 0 to 2 mA for the electrode e2, and 2 to 3 mA for the electrode e3 (if the source S1 is cathodic, and the source S2 is anodic), or a current range of 1 to 2 mA for the electrode e1, −2 to 0 mA for the electrode e2, and −2 to −3 mA for the electrode e3 (if the source S1 is anodic, and the source S2 is cathodic) (FIG. 12g).

It should be noted that although the above-described embodiments illustrate and describe the current sources S1, S2 as having different current values or different current ranges, which provides greater variability in the current values, the current sources S1, S2 may have the same current values or the same current ranges. Furthermore, it should be noted that the above current values and ranges on the electrodes e1, e2, e3 assume a uniform impedance at the electrodes e1, e2, e3. In actuality, the impedances at the electrodes e1, e2, e3 will vary from each other due to the different tissue impedances. As such, the current values at the electrodes e1, e2, e3 may vary from the theoretical current values. However, because the monitoring circuitry 72 can be utilized to measure the impedances at the electrodes e1, e2, e3, the processing circuitry (e.g., the microprocessor 76), utilizing simple voltage models, can compute the actual current values or ranges on the electrodes e1, e2, e3 from the known current values or ranges output by the sources S1, S2 and the measured impedances at the electrodes e1, e2, e3. Furthermore, although only two sources S1, S2 are described with respect to FIGS. 11 and 12, more than two sources can be coupled to subsets of the electrodes to provide many more different combinations of current values on larger sets of electrodes.

Figure 13:
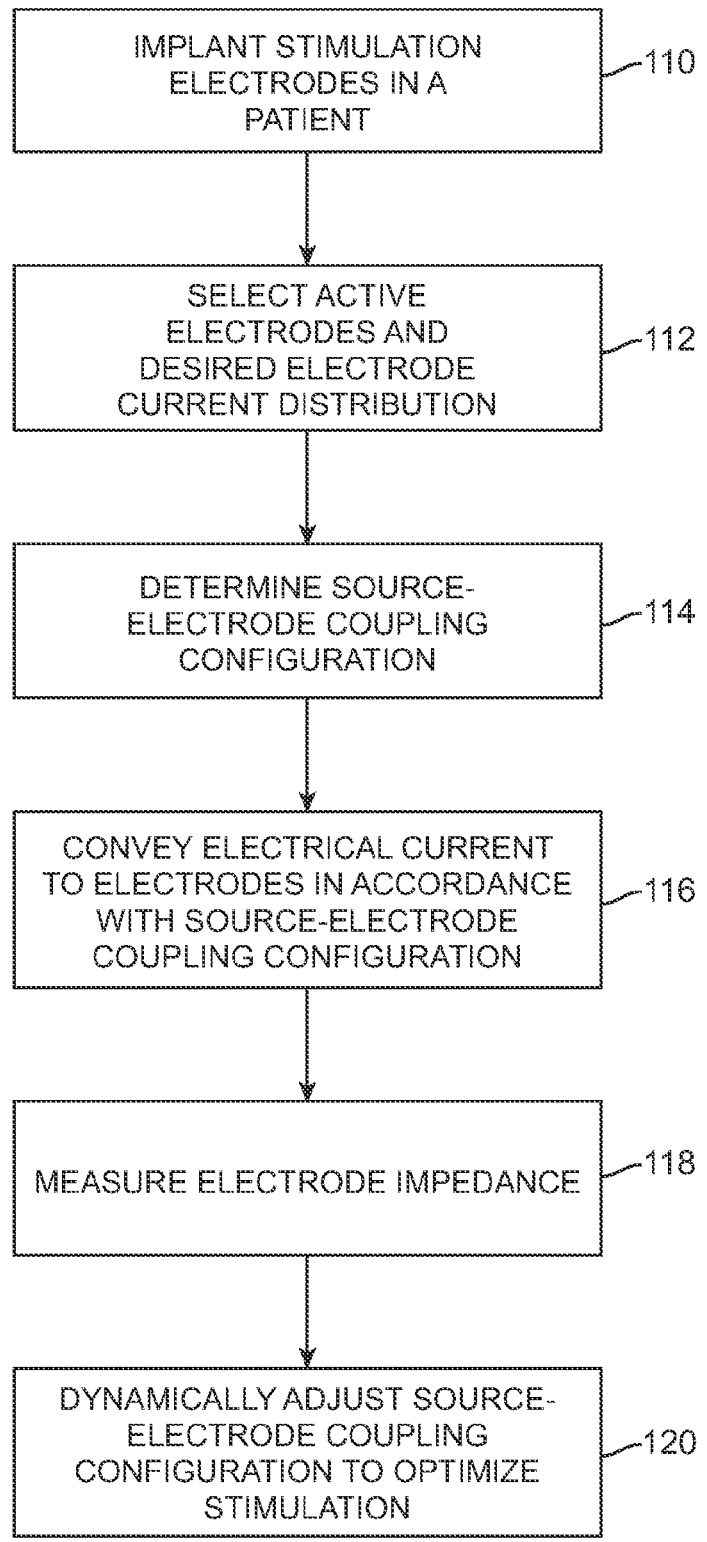
FIG. 13 is a flow diagram illustrating a method for utilizing source combination to implement a desired current distribution using a relatively small number of sources.

Referring to FIG. 13, a method of utilizing the SCS system 10 will now be described. First, the electrode leads 12 are implanted into the patient 40, as shown in FIG. 5 (block 110). Then, the RC 16 and/or CP 18 may be operated to select the combination of the electrodes 26 to be activated and the electrical current values on the activated electrodes 26 (i.e., the electrode current distribution), and in this embodiment, to select the fractionalized current values for the electrodes 26 and to globally vary the current on the activated electrodes 26 to obtain the desired current values (block 112). The source-electrode coupling configuration that best meets the desired current values can then be determined (block 114). Such determination may be accomplished in various ways, including minimizing the total absolute current error on each selected electrode, minimizing the total current electrode in the cathodes (even if it means higher error in the anodes), finding a configuration that meets an error level that does not exceed a particular maximum error level, minimizing the maximum absolute current error on each electrode without exceeding a particular absolute (mA) or relative (%) error for any given electrode, etc.

Notably, the source-electrode coupling configuration that best meets the desired fractionalized current values may be determined, and then, the current to be output by the sources 60 may be globally scaled up or down to match the desired absolute current values on the electrodes 26. Inputs to this process may be toleranced for matching the desired current values on the electrodes 26. For example, the target current values may require that each of two electrodes convey cathodic current at 3 mA plus or minus 0.2 mA, and an additional three electrodes convey cathodic current at 2 mA plus or minus 0.4 mA. Notably, in the case where reconfigurable current sources are used, at least one of the current sources may be reconfigured from a second polarity to a first polarity (e.g., reconfigured from a cathodic source to an anodic source, or vice versa) in accordance with the source-electrode coupling configuration.

Subsequent to determination of the source-electrode coupling configuration, electrical current is conveyed between active ones of the current sources 60 and active subsets of the electrodes 26 in accordance with the determined source-electrode coupling configuration (block 116). In some cases, portions of, or all, of the current conveyed from some of the sources 60 will be combined in an additive manner (if the sources are of the same polarity) and/or a subtractive manner (if the sources are of different polarities) to produce a combined electrical current that is conveyed to or from at least one of the electrodes, e.g., in the manner illustrated with respect to the electrodes e1, e2, e3 in the source-electrode coupling configurations illustrated in FIGS. 11c and 11d, or the electrode e2 in the source-electrode configuration illustrated in FIG. 11f. Significantly, in all cases illustrated in FIGS. 11a-11g, the total number of active electrodes (three) exceeds the total number of active sources (two), thereby minimizing the number of sources needed to drive the electrodes.

In making the source-electrode coupling configuration determination, the impedance at the electrodes to be activated may be assumed or measured and utilized to provide the best fit. Impedance measurements are especially significant when electrical current is to be conveyed from a source to multiple electrodes. Even if a current source is used in this case, the impedances on the electrodes coupled to the current source may be different, thereby creating a voltage divider network that will create an unequal split in the partial currents supplied to the electrodes. Using basic known voltage divider calculations, however, the magnitudes of the respective partial currents can be determined based on the magnitude of the current source output and the impedances.

Thus, the impedances can be subsequently measured (block 118), and this information may be utilized to tune, or dynamically adjust, the source-electrode coupling configuration to optimize electrical stimulation treatment (block 120). If reconfigurable current sources are used, at least one of the current sources may be reconfigured from the first polarity back to the second polarity in accordance with the new or adjusted source-electrode coupling configuration if necessary. In any event, all or portions of the current conveyed from some of the sources 60 may be combined in an additive manner and/or a subtractive manner to produce another combined electrical current that is conveyed to or from one of the electrodes. The sources used to generate the previously combined electrical current and the sources used to generate the subsequently combined electrical current can be associated can be the same or different, and the electrode(s) to or from which the previously combined electrical current is conveyed and the electrode(s) to or from which the subsequently combined electrical current is conveyed can be the same or different.

Control of the various aspects of the process described in reference to FIG. 13 may be accomplished in a variety of manners and performed by either the IPG 14 in an "on-board processing" configuration, by an external control device (such as, e.g., the RC 16 and/or CP 18) in an "off-board processing" configuration, or with combinations thereof. For example, in one off-board processing embodiment, the external control device may be configured to wirelessly transmit a command to the IPG 14 to measure the tissue resistances or impedances within the current branches associated with the activated electrodes 26 to assist with the selection of a desired stimulation schema. In such a configuration, the forward telemetry circuitry 80 receives the command, and the monitoring circuitry 58, under control by the microcontroller 76, measures the tissue resistances or impedances. The back telemetry circuitry 76, under control by the microcontroller 76, then wirelessly transmits the measured tissue resistances or impedances back to the external control device. Based on the measured values, the external control device may be configured to not only assist with selecting the electrodes to be activated and the desired current values on the activated electrodes, hardware configuration, and other input, but also to compute the source-electrode coupling configuration, or variation thereto, which would optimize the stimulation under the desired electrical stimulation schema. The external control device may then wirelessly transmit a control signal containing updated stimulation parameters, including the source-electrode coupling configuration, to the IPG 14. The forward telemetry circuitry 80, under control by the microcontroller 76, receives the control signal, and the analog output circuitry 50, including the switch 90, under control of the microcontroller 76, adjusts the source-electrode coupling to the desired configuration.

In another embodiment having at least some on-board processing for determining the source-electrode coupling configuration, the external control device wirelessly transmits a control signal containing the desired electrical stimulation parameters, including desired current values at the activated electrodes 26, to the IPG 14. The forward telemetry circuitry 80, under control by the microcontroller 76, receives the control signal, and the microcontroller 76, based on measured tissue resistances or impedances (performed by the monitoring circuitry 58 either prior to or after receipt of the control signal), may determine the source-electrode coupling configuration needed to obtain the desired fractionalized currents at the activated electrodes 26. In other words, the determination of the source-electrode coupling configuration is handled on-board with the microcontroller 76. The analog output circuitry 50, including the switch 90, under control of the microcontroller 76, then adjusts the source-electrode coupling to the desired configuration.

Alternatively, rather than determining the source-electrode coupling configuration through computational means, the monitoring circuitry 58 may measure the electrical current at the activated electrodes 26, and the analog output circuitry 50, under control of the microcontroller 76, can modify the source-electrode coupling configuration until the measured electrical currents at the activated electrodes 26 match the desired electrical current values. In either case, the microcontroller 76 may either vary the source-electrode coupling configuration to achieve the desired electrical current distribution only in response to a command received by the external control device, or may periodically monitor the electrical currents at the activated electrodes 26 and adjust the source-electrode coupling configuration, if needed, to maintain the desired electrical current distribution at the activated electrodes 102 in a closed loop fashion.

It should be noted that the above techniques for using combined sources can be used in the ETS 20. In this case, electrical current, under control of the ETS 20 and external control device, can be steered between the electrodes to determine one or more sets of stimulation parameters that provide effective therapy to the patient. The current distribution can either be measured in the ETS or estimated based on the effective resistances. Once the stimulation parameter sets, including the effective current distributions, are determined, they can be programmed into the IPG in the form of a source-electrode coupling configuration. This technique may be particularly advantageous when the IPG has minimal or no computer power, which may otherwise be needed to perform the techniques described herein.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
   a plurality of electrical terminals configured for being coupled to a respective plurality of electrodes;
   a plurality of electrical sources;
   processing circuitry configured for determining a source-electrode coupling configuration from the electrical sources and electrodes; and
   control circuitry configured for respectively conveying electrical current between active ones of the plurality of electrical sources and active subsets of the plurality of electrodes at the same time in accordance with the determined source-electrode coupling configuration, wherein at least two of the active electrode subsets include at least one common electrode, and the total number of the electrodes in the active electrode subsets is greater than the total number of the active electrical sources,
   wherein at least two of the active electrode subsets do not include a common electrode.

2. A method of providing therapy to a patient implanted with a plurality of electrodes using a plurality of electrical sources, the method comprising:
   determining a source-electrode coupling configuration from the electrical sources and electrodes; and
   respectively conveying electrical current between active ones of the plurality of electrical sources and active subsets of the plurality of electrodes at the same time in accordance with the determined source-electrode coupling configuration, wherein at least two of the active electrode subsets include at least one common electrode, and the total number of the electrodes in the active electrode subsets is greater than the total number of the active electrical sources,
   wherein at least two of the active electrode subsets do not include a common electrode.

* * * * *